United States Patent [19]

Elliott

[11] Plant 4,892

[45] Oct. 5, 1982

[54] ROSE PLANT

[76] Inventor: Charles P. Elliott, 2208 Monterey Ave., Santa Clara, Calif. 95051

[21] Appl. No.: 229,771

[22] Filed: Jan. 29, 1981

[51] Int. Cl.[3] ..... A01H 5/00

[52] U.S. Cl. ..... Plt./28

[58] Field of Search ..... Plt./19–20, Plt./27–28

*Primary Examiner*—Robert E. Bagwill

*Attorney, Agent, or Firm*—Thomas E. Schatzel

[57] ABSTRACT

A new variety of rose plant originating as a cross between an unnamed seed parent derived from a cross between Baccarra and Garnet and an unknown pollen parent by open pollination and characterized by its small ruffled red-pink blooms, vigorous growth and persistence.

2 Drawing Figures

BACKGROUND OF THE NEW PLANT

The present invention comprises a new and distinct cultivar of rose plant which is a seedling cross-bred in Santa Clara, Calif. The new seedling was initially produced by open pollination of a seed parent which was derived as a cross between Baccara and Red Garnet. It is believed that the new seedling is probably the result of self pollination of the seed parent. The new seedling is a hybrid rose (Floribunda) which has been named "Sacajawea" by the inventor. The new seedling was selected from the offspring of the aforementioned cross in Santa Clara, Calif. and has been asexually reproduced by bud grafting at Santa Clara, Calif. and Newman, Calif. The new seedling has been found to retain its distinctive characteristics through successive propagations.

DESCRIPTION OF THE DRAWING

The accompanying drawing shows the unique characteristics of the new seedling, the color being as nearly true as possible with color illustrations of this type. The photographs show the bloom and the foliage of the new seedling.

DESCRIPTION OF THE NEW PLANT

The new seedling is a hybrid (Floribunda) rose with a bright uniformly red-pink bloom. The seedling has been grown under outdoor and greenhouse conditions in the vicinity of Watsonville, Calif. and under outdoor conditions in Pierce County, Washington and has been found to have a repeating spring to fall blooming pattern under these conditions.

The new seedling is similar in some respects to the rose variety known as Garnette, a well known commercial variety, and has generally the same characteristics and the Garnet in so far as:

1. Height of plant.
2. Upright stature of plant.
3. Vigorous growth characteristics.
4. Small, singly and multiple borne blooms.
5. Abundant foliage.
6. Overall color of foliage.
7. Foliage shape.
8. Overall plant size.
9. Good persistence of petals.
10. Shape of reproductive organs.
11. Very slight bloom fragrance.

The new seedling is distinguished from the Garnet variety by the following characteristics.

1. Foliage has different underside color.
2. The bloom size is smaller.
3. The bloom color is more pink.
4. The petals are ruffled rather than short and double.
5. The petals are not spirally arrayed but are irregular.
6. The stamens are more orange than yellow.

In the description which follows, color references are made to the Horticultural Colour Chart, Volumes I and II, issued by the British Colour Council in collaboration with the Royal Horticultural Society and copyrighted 1939 and 1941.

Botanical Classification: *Rosa hybrida.*

Bud:

*Size.*—Small.

*Form.*—Short, with flat top, minimally affected by wet or hot weather.

*Sepals.*—Hooded above bud to a point, smooth edges.

*Calyx.*—Small, smooth, funnel shaped, slight apple color.

*Peduncle.*—Short, erect.

Color:

*Initial sepal division.*—Currant Red 821/1.

*Initial unfurling.*—Cardinal Red 822.

*Half blown; inside of petals.*—Jasper Red o18.

*Half blown; reverse of petals.*—Blood Red 820/3.

Bloom:

*Size.*—Small, approx. 1¾" when fully expanded.

*Borne.*—Singly in flat clusters.

*Stems.*—Short, normal.

*Form.*—Cupped.

*Permanence.*—Flattens.

Color:

*Center of flower.*—Jasper Red o18.

*Base of petals.*—White.

*Inside of petals.*—Jasper Red o18.

*Reverse of petals.*—Rose Opal o22/1.

*Tonality from distance.*—Jasper Red o18.

Petals:

*Texture.*—Thick.

*Appearance.*—Ruffled, satiny, round.

*Arrangement.*—Double, irregular, few petaloids in center.

*Persistence.*—Hang on and dry.

*Fragrance.*—Very slight.

Reproductive organs:

*Stamens, anthers.*—Small, many, Orange Buff 507, arranged regularly around styles.

*Stamens, filaments.*—Short threads, various colors: e.g. Jasper Red o18/3, Straw Yellow 604/3 and Dresden Yellow $64_3$.

*Styles.*—Bunched, short.

*Stigmas.*—Uranium Green 63/3.

Plant:

*Form.*—Bush.

*Growth.*—Vigorous, upright.

*Height.*—Approximately 0.9 meters (3 feet).

*Spread.*—Approximately 0.5 meters (19 inches).

Foliage:

*Leaflets.*—Groups of five, medium size, normal abundancy.

*Top side of new foliage.*—Purple Madder o281.

*Under side.*—Pansy Purple 928/3.

*Shape.*—Pointed oval.

*Texture.*—Smooth.

*Ribs and veins.*—Light.

*Edge.*—Serrated.

*Serrations.*—Small.

*Stipules.*—Medium.

*Leaf stem.*—Spinach Green o960/2.

*Disease resistance.*—Susceptible to mildew.

Thorns:

*Quantity.*—Irregular, varying from many on some main stalks to few on others, few on lateral stalks.

*Form.*—Flat base, medium length hooked downward.

*Color when young.*—Spinel Red oo23 to Olive Green o62/2.

*Position.*—Random.

I claim:

1. A new and distinct cultivar of rose, substantially as described and pictured herein, characterized by its small ruffled red-pink blooms, vigorous growth and persistence.

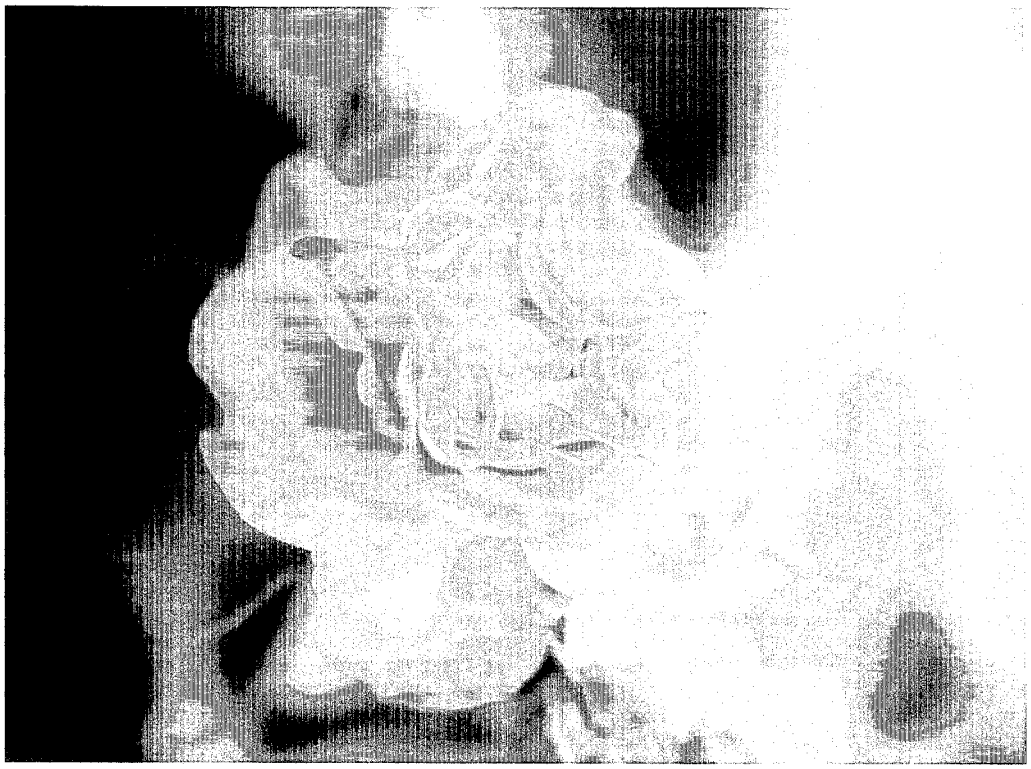
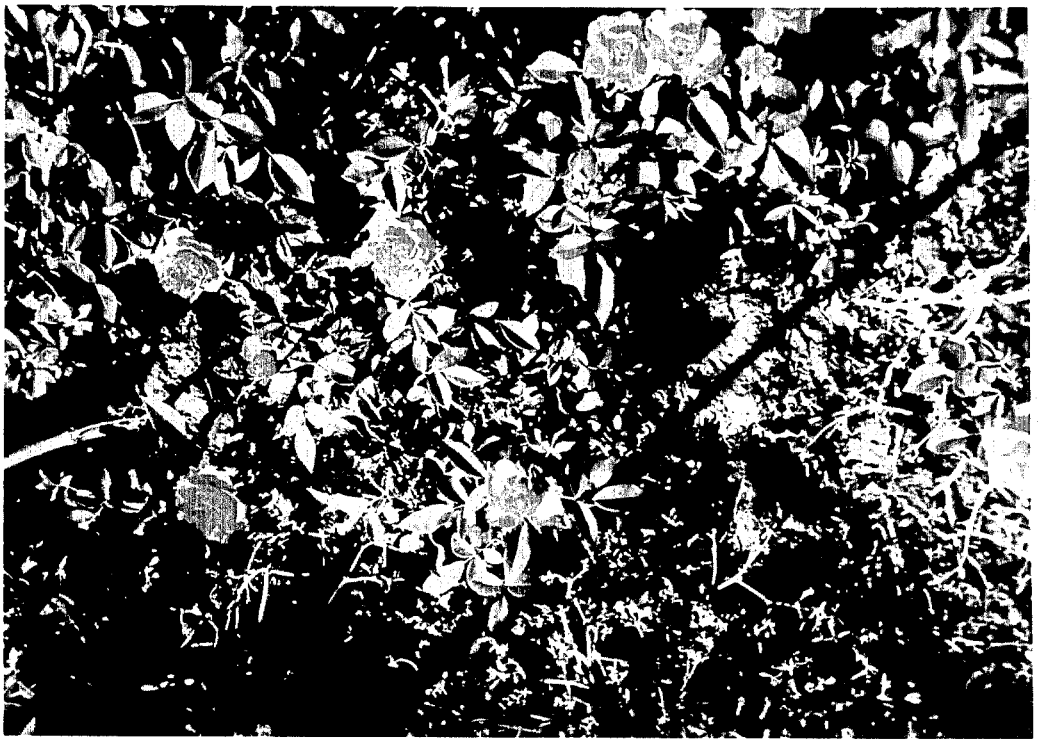

* * * * *